US006668617B2

United States Patent
Radu et al.

(10) Patent No.: US 6,668,617 B2
(45) Date of Patent: Dec. 30, 2003

(54) 02 SENSOR FILTER

(75) Inventors: Richard A Radu, Grand Blanc, MI (US); Robert J Nankee, II, Canton, MI (US); William P Eichbrecht, Livonia, MI (US); Leon O Cribbins, Farmington, MI (US); Joseph J Kopera, Jr., Trenton, MI (US); George C Mitchell, Brighton, MI (US)

(73) Assignee: DaimlerChrysler Corporation, Auburn Hills, MI (US)

(*) Notice: Subject to any disclaimer, the term of this patent is extended or adjusted under 35 U.S.C. 154(b) by 210 days.

(21) Appl. No.: 09/920,055

(22) Filed: Aug. 1, 2001

(65) Prior Publication Data

US 2003/0024296 A1 Feb. 6, 2003

(51) Int. Cl.$^7$ .................. G01N 33/00; G01M 15/00
(52) U.S. Cl. .................. 73/23.32; 73/118.1
(58) Field of Search .................. 73/23.31, 23.32, 73/118.1, 1.06; 701/109, 99, 101, 102

(56) References Cited

U.S. PATENT DOCUMENTS

| 4,122,811 A | * | 10/1978 | Bowler et al. ............ 123/696 |
| 4,191,151 A | * | 3/1980 | Wanamaker ............ 123/694 |
| 4,462,373 A | * | 7/1984 | Kanno ............ 123/489 |
| 4,957,087 A | * | 9/1990 | Ota ............ 123/479 |
| 5,090,389 A | * | 2/1992 | Oota ............ 123/685 |
| 5,325,711 A | * | 7/1994 | Hamburg et al. ............ 73/118.1 |
| 5,363,646 A | * | 11/1994 | Orzel et al. ............ 60/274 |
| 5,372,036 A | * | 12/1994 | Kainz ............ 73/117.3 |
| 5,544,481 A | * | 8/1996 | Davey et al. ............ 60/274 |
| 5,579,746 A | * | 12/1996 | Hamburg et al. ............ 123/689 |
| 5,826,426 A | | 10/1998 | Weber et al. ............ 60/274 |
| 5,983,877 A | * | 11/1999 | Madugula et al. ............ 701/109 X |
| 6,481,427 B1 | * | 11/2002 | Javaherian ............ 123/673 |
| 2002/0134362 A1 | * | 9/2002 | Deutscl ............ 123/575 |

FOREIGN PATENT DOCUMENTS

| JP | 4-91339 | * | 3/1992 | ............ 123/350 |
| JP | 6-207510 | * | 7/1994 | ............ F02D/41/14 |

* cited by examiner

Primary Examiner—Thomas P. Noland
(74) Attorney, Agent, or Firm—Edwin W. Bacon, Jr.

(57) ABSTRACT

A method of filtering an oxygen sensor signal is provided. The method includes obtaining the oxygen sensor signal from the oxygen sensor on a periodic basis. The oxygen sensor signal is then compared to an average oxygen sensor signal value. If the oxygen sensor signal is greater than the average oxygen sensor signal value, a high signal counter is incremented. If the high signal counter is greater than a high signal count threshold, the oxygen sensor signal is forced to a high signal value. If the oxygen sensor signal is less than the average oxygen sensor signal value, a low signal counter is incremented. If the low signal counter is greater than a low signal count threshold, the oxygen sensor signal is forced to the low signal value. The high and low signal count thresholds correspond to a preselected period of time indicating a low or high signal trend within the oxygen sensor signal.

8 Claims, 3 Drawing Sheets

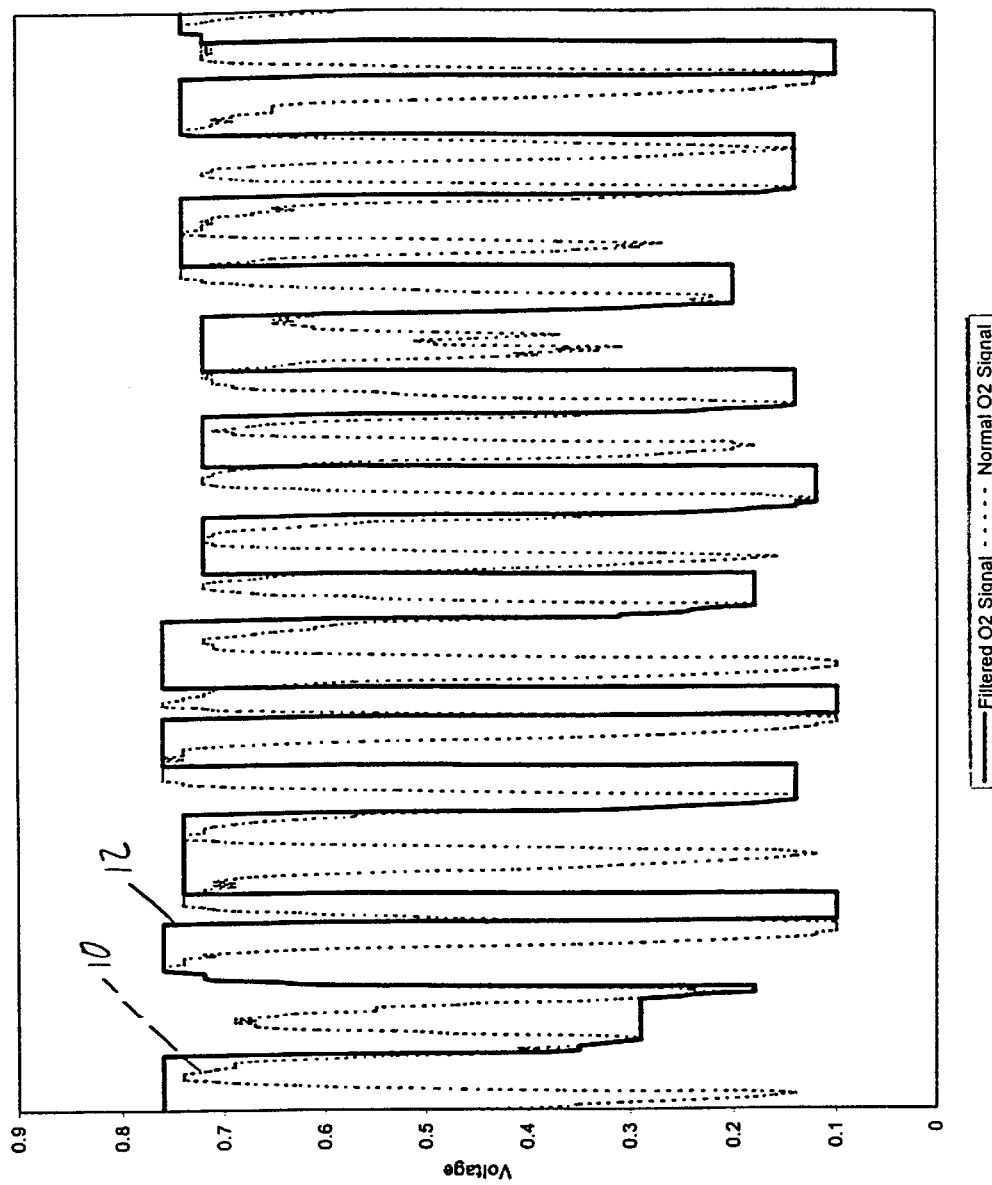

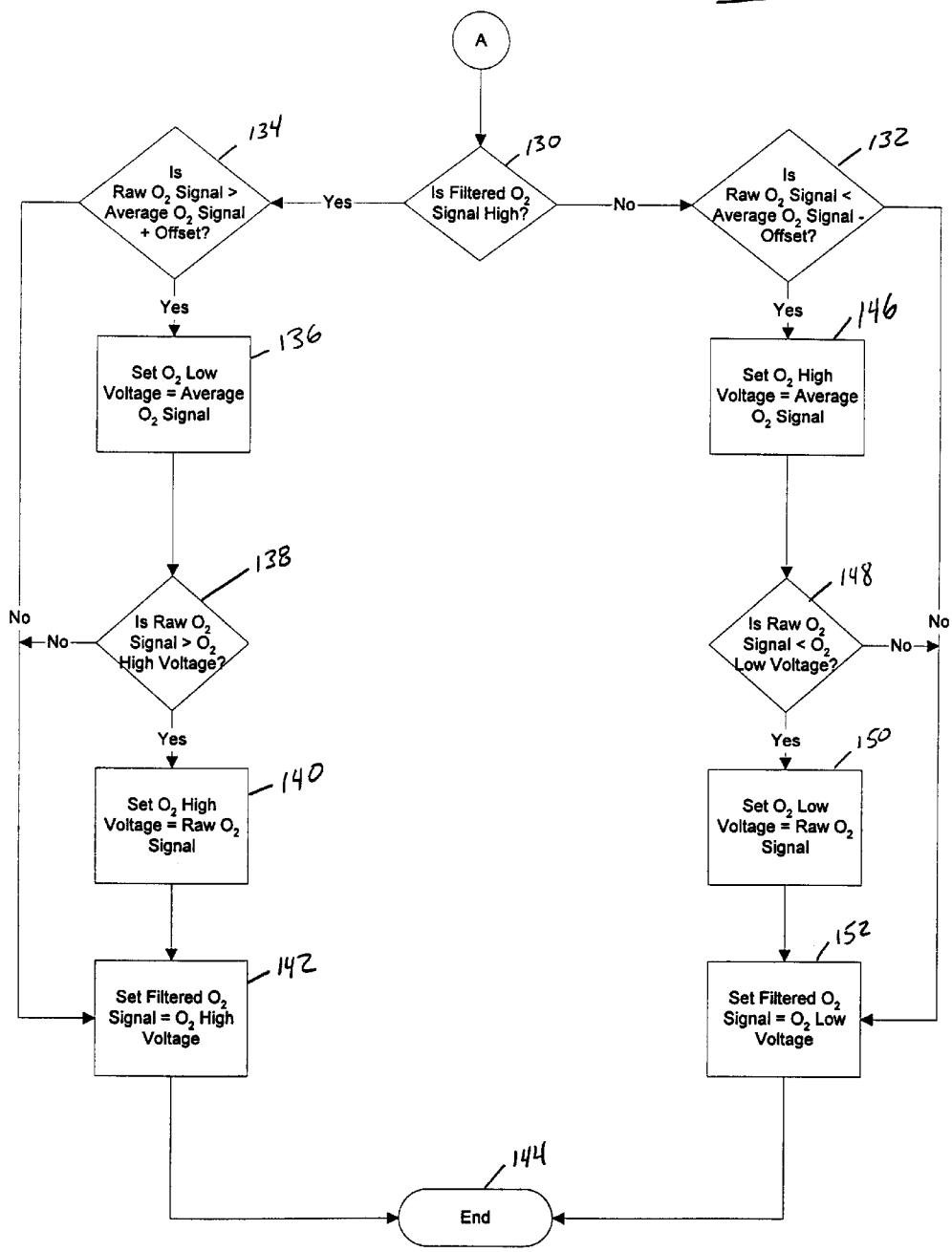

O2 SENSOR FILTER

BACKGROUND OF THE INVENTION

1. Technical Field

The present invention generally relates to oxygen sensor signal filtering and, more particularly, to a method of selectively forcing an oxygen sensor signal to a high or low signal state.

2. Discussion

Modern automotive vehicles are commonly equipped with oxygen sensors in the exhaust system. The oxygen sensors indicate a lean or rich operating condition by sensing the amount of oxygen in the emissions. Switching type oxygen sensors provide a voltage which is either low or high depending upon the amount of oxygen in the system.

A switching type oxygen sensor emits a low voltage signal under a lean condition and a high voltage signal under a rich condition. Depending upon the signal received from the oxygen sensor, the engine controller can vary the fuel to air ratio within the vehicle engine to vary the emissions output. As such, closed loop or feedback control is established.

The sensitivity of modern oxygen sensors allows detection of lean and rich conditions at an extremely high frequency. For example, modern oxygen sensors can sense the varying conditions within the emissions caused by individual cylinder firing events. Since such switching is not associated with the true chemical condition of the emissions, the type of switching is commonly known in the art as chemical noise.

Chemical noise causes the output of the oxygen sensor to be somewhat unreliable. That is, the oxygen sensor may switch between low and high voltage signal states due to an individual cylinder firing event where over a greater time period the true condition of the emissions may not be accurately reflected in the signal. Such "false" switching may lead to a variation in the fueling of the engine which would otherwise be unnecessary.

Conventional attempts to reduce false switching include changing the frequency of the oxygen sensor signal and also filtering out voltage spikes. One such attempt averages the input of the oxygen sensor signal. By slowing down the filter rate, the output signal experiences a change in frequency and a decrease in noise level. Unfortunately, such output signals are too slow for most operating systems. As such, the system can not reliably detect sensor signal switching between a low signal state and a high signal state.

Another attempt to reduce false switching involves the detection of the slope of the input signal. When enough of a positive slope is detected, the output signal is forced high. When enough of a negative slope is detected, the output signal is forced low. Unfortunately, the output signal still has noise in it and this technique does not have a significant impact on the frequency of the oxygen sensor signal.

In view of the forgoing, there continues to be a need in the art for a method of filtering an oxygen sensor signal so that reliable switching between the low and high voltage signal states can be readily detected.

SUMMARY OF THE INVENTION

The above and other objects are provided by a method of filtering an oxygen sensor signal. The method includes obtaining an oxygen sensor signal from the oxygen sensor on a periodic basis. The oxygen sensor signal is then compared to the average oxygen signal voltage. If the oxygen sensor signal is greater than the average oxygen signal voltage, a high signal counter is incremented. If the high signal counter is greater than a signal count threshold, the oxygen sensor signal is forced to a high signal value. If the oxygen sensor signal is less than the average oxygen signal voltage, a low signal counter is incremented. If the low signal counter is greater than a signal count threshold, the oxygen sensor signal is forced to a low signal value. The high and low signal count thresholds correspond to a preselected period of time indicating a low or high signal trend within the oxygen sensor signal.

BRIEF DESCRIPTION OF THE DRAWINGS

The various advantages of the present invention will become apparent to one skilled in the art upon reading the following specification and by reference to the drawings in which:

FIG. 1 is a graph illustrating the oxygen sensor voltage signal over a period of time and a filtered oxygen sensor signal over the same period of time; and FIGS. 2a and 2b are flowcharts illustrating the methodology of the present invention.

DETAILED DESCRIPTION OF THE PREFERRED EMBODIMENTS

Figure 2A:
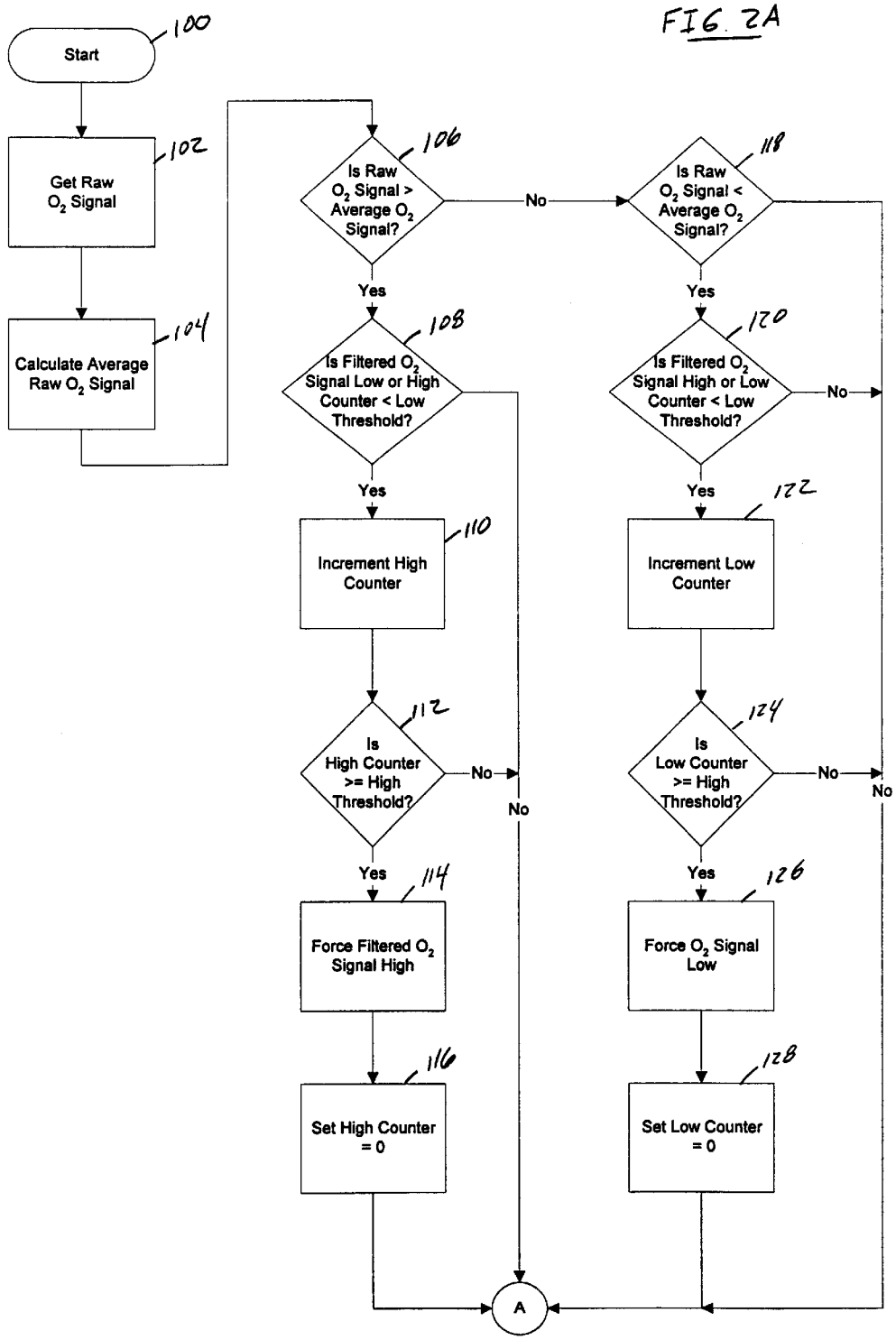

The present invention is directed towards filtering an oxygen sensor signal to reduce the noise within the signal and reduce the number of detected false switches. The methodology forces the oxygen sensor signal to a high signal value if the oxygen sensor signal is greater than an average oxygen signal value over a preselected period of time. The oxygen sensor signal is forced to a low signal value if the oxygen sensor signal is less than the average oxygen signal value over a preselected period of time. Since a preselected period of time elapses prior to accepting the oxygen sensor signal as reliable, fewer false switches are detected and noise within the signal is reduced. For the purpose of this description, a raw oxygen sensor signal refers to the raw voltage produced by an oxygen sensor as it measures the varying air to fuel ratio in the exhaust gas stream of a vehicle. A filtered oxygen sensor signal refers to the output of the method described and which is used in a vehicle in place of the raw oxygen sensor voltage to modify the fuel to air ratio delivered for combustion.

Turning now to the drawing figures, FIG. 1 illustrates a raw (i.e., unfiltered) oxygen sensor signal output 10 and a filtered oxygen sensor signal 12 over time. As can be seen, the raw oxygen sensor signal 10 switches between a low state from about 0.1 to about 0.3 volts and a high state from about 0.6 to about 0.8 volts over time. This is because the emissions detected by the oxygen sensor producing the raw signal 10 are varying between a lean and rich condition. As will be described in greater detail below, the methodology of the present invention filters the raw oxygen sensor signal 10 so as to produce the filtered oxygen sensor signal 12. As can be seen, the frequency of the filtered oxygen sensor signal 12 is much slower than the frequency of the raw oxygen sensor signal 10. Further, the peaks and valleys of the filtered oxygen sensor signal 12 are more consistent than the peaks and valleys of the raw oxygen sensor signal 10. In addition, the demarcation between the peaks and valleys of the filtered oxygen sensor signal 12 is more clear than between the peaks and valleys of the raw oxygen sensor signal 10.

Turning now to FIG. 2, the methodology for producing the filtered oxygen sensor signal 12 of FIG. 1 is illustrated.

The methodology begins at bubble 100 and falls through to block 102. Preferably, the methodology is performed periodically such as every 11 ms or every engine cycle.

In block 102, the methodology obtains the raw oxygen sensor signal from an oxygen sensor associated with the exhaust system of the vehicle in which the methodology is employed. The raw oxygen sensor signal may be produced by any one of a number of oxygen sensors disposed along a conventional exhaust system. As one skilled in the art will readily appreciate, the amount of filtering required for the individual output of any given oxygen sensor depends upon the location of that oxygen sensor within the exhaust system and the particular oxygen sensor employed.

After obtaining the oxygen sensor signal at block 102, the methodology continues to block 104. In block 104, the methodology determines the average raw oxygen sensor signal. To accomplish this, a filter value is selected, for example, a 10% filter. With this filter value, the average raw oxygen sensor signal is calculated by multiplying the raw oxygen sensor signal obtained in block 102 by 10% and adding to this 90% of the average raw oxygen sensor signal calculated in block 104 from the previous loop (in this example, the value of the average raw oxygen sensor signal from 11 ms ago). In other words: New average=(100%−filter factor)×Old average+filter factor×Raw 02 signal.

After determining the average raw oxygen sensor signal value in block 104, the methodology continues to decision block 106. In decision block 106, the methodology determines whether the current raw oxygen sensor signal value obtained at block 102 is greater than the average oxygen sensor signal value determined at block 104. The average oxygen sensor signal value provides a demarcation between a high voltage signal state and a low signal state of the oxygen sensor.

If the raw oxygen sensor signal is greater than the average oxygen sensor signal value at decision block 106, the methodology continues to decision block 108. In decision block 108, the methodology determines whether a filtered oxygen signal (described below) has been set equal to a low voltage level or whether a high sensor signal value counter (also described below) is less than a low threshold value. This low threshold value may be set equal to the number of consecutive readings desired for deeming the sensor signal to be in a low regime such as, for example, 2.

If the filtered oxygen signal is not low and the high counter is not less than the low threshold at decision block 108, the methodology advances through connector A to FIG. 2B. On the other hand, if the filtered oxygen sensor signal is low, or if the high counter is less than the low counter threshold, the methodology advances to block 110. In block 110, the methodology increments a high sensor signal voltage counter.

After incrementing the high sensor signal voltage counter at block 110, the methodology continues to decision block 112. In decision block 112 the methodology determines whether the high counter is greater than or equal to a high counter threshold. The high counter threshold value preferably corresponds to an amount of time sufficient to ensure a reliable signal. This time preferably equals about 66 ms which may be tabulated by a timer or by counting process loops. If loops are used, the high counter threshold value is equal to 6.

If the high sensor signal voltage counter is less than the high counter threshold at decision block 112, the methodology advances through connector A to FIG. 2B. On the other hand, if the high sensor signal voltage counter is greater than or equal to the high counter threshold at decision block 112, the methodology continues to block 114. In block 114, the methodology forces the filtered oxygen sensor signal to a high sensor value. Preferably, the high sensor value corresponds to the most recent high peak of the raw oxygen sensor signal value. Alternatively, the high sensor signal voltage may be set equal to a preselected voltage value such as 0.75 volts.

After forcing the oxygen sensor signal to a high value at block 114, the methodology continues to block 116. In block 116, the methodology sets the high counter value equal to zero. From block 116, the methodology advances through connector A to FIG. 2B.

Referring again to decision block 106, if the raw oxygen sensor signal is less than or equal to the average oxygen sensor signal value, the methodology continues to decision block 118. In decision block 118, the methodology determines whether the raw oxygen sensor signal is less than the average oxygen sensor signal value.

If the oxygen sensor signal is equal to the average oxygen sensor signal at decision block 118 (note that it won't be greater than since this condition was filtered out at decision block 106), the methodology advances through connector A to FIG. 2B. On the other hand, if the oxygen sensor signal value is less than the average oxygen sensor signal value at decision block 118, the methodology continues to decision block 120.

In decision block 120, the methodology determines whether the filtered oxygen sensor signal is equal to an oxygen sensor signal high voltage value, or whether the low counter is less than a low counter threshold value. The low counter threshold value is preferably equal to that used in decision block 108, or, for example, 2.

If the filtered oxygen sensor signal value is not high, or if the low counter value is great than or equal to the low threshold value, the methodology advances through connector A to FIG. B.

On the other hand, if the filtered oxygen sensor signal is high, or if the low counter is less than the low counter threshold value, the methodology continues to block 122. In block 122, the methodology increments the low sensor signal counter. After incrementing the low sensor signal counter at block 122, the methodology continues to decision block 124.

In decision block 124, the methodology determines whether the low counter is greater than or equal to a high counter threshold. The high counter threshold value preferably corresponds to an amount of time sufficient to ensure a reliable signal. This time preferably equals about 66 ms which may be tabulated by a timer or by counting process loops. If loops are used, the high voltage counter threshold value is equal to 6.

If the low sensor signal voltage counter is less than the high counter threshold at decision block 124, the methodology advances through connector A to FIG. 2B. On the other hand, if the low sensor signal voltage counter is greater than or equal to the high voltage counter threshold at decision block 124, the methodology continues to block 126. In block 126, the methodology forces the filtered oxygen sensor signal to a low sensor value. Preferably, the low sensor value corresponds to the most recent low peak of the raw oxygen sensor signal value. Alternatively, the low sensor signal voltage may be set equal to a preselected voltage value such as 0.1 volts.

After forcing the raw oxygen sensor signal to a low value at block 126, the methodology continues to block 128. In block 128, the methodology sets the low counter value equal to zero. From block 128, the methodology advances through connector A to FIG. 2B.

Referring now to FIG. 2B, the methodology continues through connector A to decision block 130. In decision block 130, the methodology determines whether the filtered oxygen sensor signal is equal to an oxygen sensor signal high voltage value. If not, the methodology advances to decision block 132. On the other hand, if the filtered oxygen sensor signal is high, the methodology continues to decision block 134.

In decision block 134, the methodology determines whether the raw oxygen sensor signal is greater than the average oxygen sensor signal plus an offset value. The offset value corresponds to a preselected tolerance range for the methodology. For example, such tolerance may be equal to 0.12 volts.

If the raw oxygen sensor signal is greater than the average oxygen sensor signal plus the offset value at decision block 134, the methodology continues to block 136. In block 136, the methodology sets the oxygen sensor low voltage value equal to the average oxygen sensor signal value. From block 136, the methodology continues to decision block 138.

In decision block 138, the methodology determines whether the raw oxygen sensor signal value is greater than the oxygen sensor signal high voltage value. If so, the methodology continues to block 140. In block 140, the methodology sets the oxygen sensor signal high voltage value equal to the raw oxygen sensor signal value.

Referring again to decision block 134, if the raw oxygen sensor signal value is not greater than the average oxygen sensor signal value plus the offset value, the methodology advances to block 142. Similarly, referring to decision block 138, if the raw oxygen sensor signal value is not greater than the oxygen sensor high voltage value, the methodology advances to block 142. Likewise, after setting the oxygen sensor high voltage value equal to the raw oxygen sensor signal value in block 140, the methodology continues to block 142.

In block 142, the methodology sets the filtered oxygen sensor signal value equal to the oxygen sensor high voltage value. From block 142, the methodology continues to terminator 144 pending a subsequent execution thereof. For example, the methodology may be run every 11 milliseconds.

Referring again to decision block 132, the methodology determines whether the raw oxygen sensor signal value is less than the average oxygen sensor signal value minus an offset value. As in decision block 134, the offset value corresponds to a tolerance for the average oxygen sensor signal. For example, 0.12 volts may be used. If the raw oxygen sensor signal is less than the average oxygen sensor signal less the offset value at decision block 132, the methodology continues to block 146. In block 146, the methodology sets the oxygen sensor high voltage value equal to the average oxygen sensor signal value.

From block 146, the methodology continues to decision block 148. In decision block 148, the methodology determines whether the raw oxygen sensor signal is less than the oxygen sensor signal low voltage value. If so, the methodology continues to block 150. In block 150, the methodology sets the oxygen sensor signal low voltage value equal to the raw oxygen sensor signal value.

Referring again to decision block 132, if the raw oxygen sensor signal value is not less than the average oxygen sensor signal value less the offset value, the methodology advances to block 152. Similarly, referring to decision block 148, if the raw oxygen sensor signal value is not less than the oxygen sensor signal low voltage value, the methodology advances to block 152. Likewise, after setting the oxygen sensor low voltage value equal to the raw oxygen sensor signal value at block 150, the methodology continues to block 152.

In block 152, the methodology sets the filtered oxygen sensor signal value equal to the oxygen sensor low voltage value. From block 152, the methodology advances to terminator 144 and ends pending a subsequent execution thereof.

Thus, a methodology is provided for forcing a raw oxygen sensor signal to a filtered high or low value depending upon the amount of time the raw oxygen sensor signal resides at a value greater than or less than an average oxygen sensor value. The slower frequency of the filtered oxygen sensor signal provides reliable control of the fueling of the engine. Moreover, much of the noise associated with an unfiltered oxygen sensor signal is removed.

Many modifications and variations of the present invention are possible in light of the above teachings. Therefore, within the scope of the appended claims, the present invention may be practiced otherwise than as specifically described.

What is claimed is:

1. A method of filtering an oxygen sensor signal comprising:

obtaining an oxygen sensor signal;

forcing said oxygen sensor signal to a high signal value if said oxygen sensor signal is greater than an average oxygen sensor signal value over a first pre-selected period of time;

incrementing a high signal counter if said oxygen sensor signal is greater than said average oxygen sensor signal;

forcing said oxygen sensor signal to said high signal value if said high signal counter is greater than a signal count threshold; and forcing said oxygen sensor signal to a low signal value if said oxygen sensor signal is less than an average oxygen sensor signal value over a second pre-selected period of time.

2. The method of claim 1 wherein said signal count threshold corresponds to said first pre-selected period of time and indicates a high voltage trend within said oxygen sensor signal.

3. The method of claim 1 wherein said step of forcing said oxygen sensor signal to said low signal value if said oxygen sensor signal is less than said average oxygen sensor signal value over said second pre-selected period of time further comprises:

incrementing a low signal counter if said oxygen sensor signal is less than said average oxygen sensor signal value and forcing said oxygen sensor signal to said low signal value if said low signal counter is greater than a signal count threshold.

4. The method of claim 3 wherein said signal count threshold corresponds to said second pre-selected period of time and indicates a low voltage trend within said oxygen sensor signal.

5. A method of filtering an oxygen sensor signal comprising:

obtaining said oxygen sensor signal;

comparing said oxygen sensor signal to an average oxygen sensor signal value;

forcing said oxygen sensor signal to a high signal value if said oxygen sensor signal is greater than said average oxygen sensor signal value over a first pre-selected period of time;

incrementing a high signal counter if said oxygen sensor signal is greater than said average oxygen sensor signal value; and forcing said oxygen sensor signal to said high signal value if said high signal counter is greater than a signal count threshold.

6. The method of claim 5 wherein said signal count threshold corresponds to said first pre-selected period of time and indicates a high voltage trend within said oxygen sensor signal.

7. A method of filtering an oxygen sensor signal comprising:

obtaining said oxygen sensor signal;

comparing said oxygen sensor signal to an average oxygen sensor signal value;

forcing said oxygen sensor signal to a high signal value if said oxygen sensor signal is greater than said average oxygen sensor signal value over a first pre-selected period of time;

forcing said oxygen sensor signal to a low signal value if said oxygen sensor signal is less than said average oxygen sensor signal value over a second pre-selected period of time;

incrementing a low signal counter if said oxygen sensor signal is less than said average oxygen sensor signal value; and forcing said oxygen sensor signal to said low signal value if said low signal counter is greater than a signal count threshold.

8. The method of claim 7 wherein said signal count threshold corresponds to said second pre-selected period of time and indicates a low voltage trend within said oxygen sensor signal.

* * * * *